United States Patent
Kim et al.

(10) Patent No.: US 11,158,401 B2
(45) Date of Patent: Oct. 26, 2021

(54) METHOD FOR SELECTING ALTERNATIVE SOLVENT

(71) Applicant: LG Chem, Ltd., Seoul (KR)

(72) Inventors: Soree Kim, Daejeon (KR); Kyoung Hoon Kim, Daejeon (KR); Seungha Kim, Daejeon (KR)

(73) Assignee: LG Chem, Ltd.

( * ) Notice: Subject to any disclaimer, the term of this patent is extended or adjusted under 35 U.S.C. 154(b) by 350 days.

(21) Appl. No.: 16/463,928

(22) PCT Filed: Jul. 23, 2018

(86) PCT No.: PCT/KR2018/008257
§ 371 (c)(1),
(2) Date: May 24, 2019

(87) PCT Pub. No.: WO2019/045274
PCT Pub. Date: Mar. 7, 2019

(65) Prior Publication Data
US 2020/0075133 A1    Mar. 5, 2020

(30) Foreign Application Priority Data

Sep. 1, 2017    (KR) .................... 10-2017-0111893

(51) Int. Cl.
*G16C 20/30*    (2019.01)
(52) U.S. Cl.
CPC .................... *G16C 20/30* (2019.02)
(58) Field of Classification Search
CPC .......... G16C 20/30; C07B 61/00; C07B 63/04
See application file for complete search history.

(56) References Cited

U.S. PATENT DOCUMENTS

| 6,231,783 | B1* | 5/2001 | Molnar | C07B 49/00 |
| | | | | 252/182.29 |
| 6,984,768 | B2* | 1/2006 | Ginosar | A62D 3/34 |
| | | | | 588/316 |
| 2005/0187408 | A1* | 8/2005 | Michalak | C07C 303/22 |
| | | | | 562/828 |
| 2009/0112486 | A1 | 4/2009 | Lustig | |
| 2015/0141532 | A1* | 5/2015 | Kim | C01B 33/152 |
| | | | | 516/104 |

(Continued)

FOREIGN PATENT DOCUMENTS

| KR | 20150022155 A | 3/2015 | |
| KR | 20170037364 A | 4/2017 | |
| WO | WO 1997/018179 A1 * | 5/1997 | C07B 49/00 |

OTHER PUBLICATIONS

Eckert et al., Fast solvent screening via quantum chemistry: COSMO-RS approach, AIChE Journal, Feb. 2002, pp. 369-385, vol. 48, Issue 2.

(Continued)

*Primary Examiner* — Tung S Lau
(74) *Attorney, Agent, or Firm* — Lerner, David, Littenberg, Krumholz & Mentlik, LLP

(57) ABSTRACT

The present invention relates to a method for selecting alternative solvents having properties similar to those of the conventionally used solvents. By simplifying the solvent selection process, it is possible to save time, effort, and resources to be consumed by complicated experiments, and the suitable solvents can be quickly selected and applied.

9 Claims, 3 Drawing Sheets

(56) References Cited

U.S. PATENT DOCUMENTS

2016/0162665 A1    6/2016  Lee et al.
2017/0083688 A1    3/2017  Chen et al.
2019/0193020 A1*  6/2019  Bara ................. B01D 53/1475

OTHER PUBLICATIONS

Klamt, Conductor-like Screening Model for Real Solvents: A New Approach to the Quantitative Calculation of Solvation Phenomena, J. Phys. Chern., Feb. 1995, pp. 2224-2235, vol. 99, No. 7.

Extended European Search Report including Written Opinion for Application No. EP18850860.0 dated Oct. 9, 2019, 5 pages.

Loschen et al., "Cosmoquick: A Novel Interface for Fast-Profile Composition and Its Application to COSMO-RS Solvent Screening Using Multiple Reference Solvents", I&EC Research, American Chemical Society, vol. 51, No. 43, Oct. 23, 2012, pp. 14303-14308.

Search report from International Application No. PCT/KR2018/008257, dated Nov. 1, 2018.

Zhou, T., et al., "Model-based Method for the Screening of Solvents for Chemical Reactions." Chemical Engineering Science, available online Nov. 19, 2013, vol. 115, pp. 177-185.

Filly, A., et al., "Alternative Solvents for Extraction of Food Aromas Experimental and COSMO-RS Study." LWT—Food Science and Technology, available online Nov. 18, 2014, vol. 61, pp. 33-40.

Garcia-Chaves, L. Y., et al., "COSMOS-RS Assisted Solvent Screening for Liquid-liquid Extraction of Mono Ethylene Blycol from Aqueous Streams." Separation and Purification Technology, available online Feb. 15, 2012, vol. 97, pp. 2-10.

Moiety, Laurianne, et al., "Panorama of sustainable solvents using the COSMO-RS approach." Green Chemistry, Published on Mar. 1, 2012, vol. 14, pp. 1132-1145.

Yara-Varón, E., et al., "Is it possible to substitute hexane with green solvents for extraction of carotenoids? A theoretical versus experimental solubility study." RSC Advances, Published on Mar. 11, 2016, vol. 6, pp. 27750-27759.

* cited by examiner

[Fig. 1]
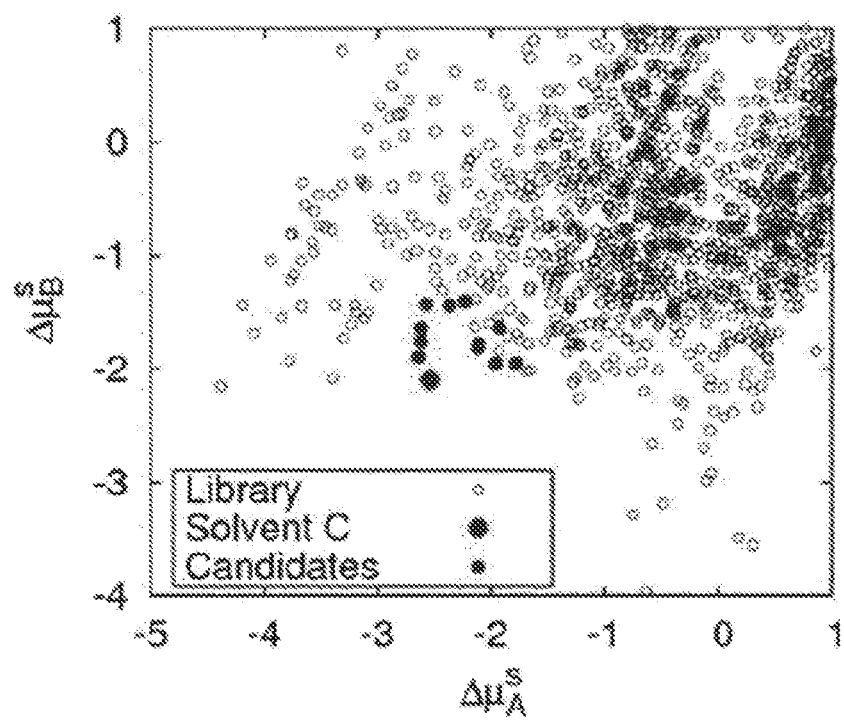

[Fig. 2]
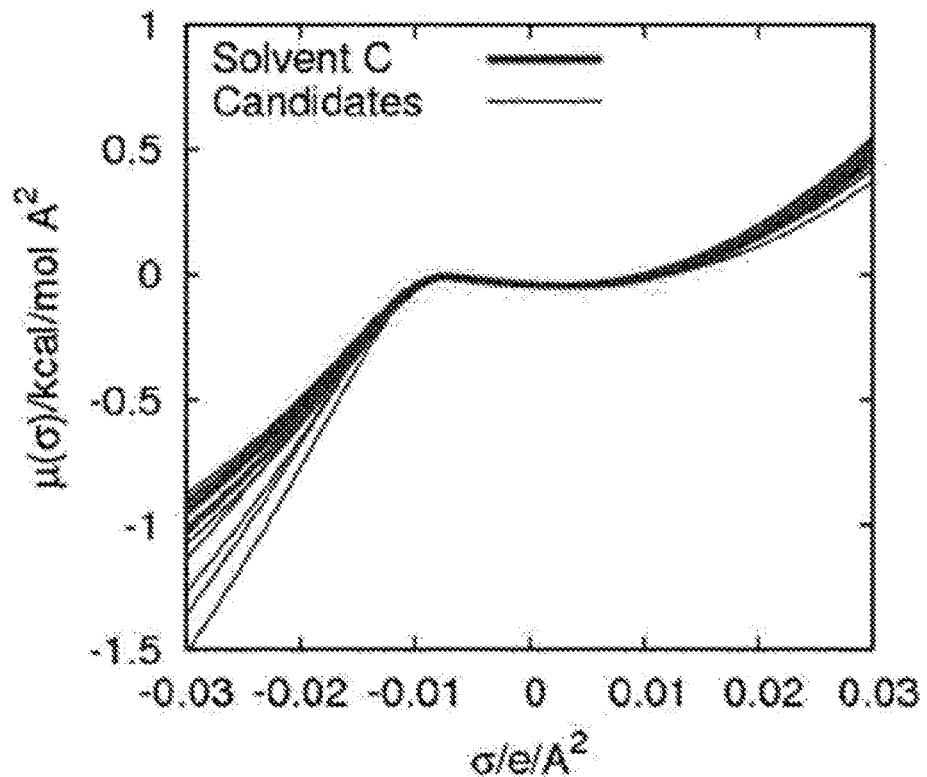

[Fig. 3]

Calculating And Standardizing A Mixing Energy Of A Reference Solvent And Solvent Candidates For A Solute

↓

Calculating a $d_{ij}$ value of the Solvent Candidates By Substituting a Similarity of the Solvent Candidates to the Reference Solvent Calculated by Using the Sigma Potentials of the Reference Solvent and the Solvent Candidates into Equation 1:

$$d_{ij} = \left|(1 - S_{ij}, \Delta\mu^s_{j1} - \Delta\mu^s_{i1}, \Delta\mu^s_{j2} - \Delta\mu^s_{i2}, \cdots, \Delta\mu^s_{jk} - \Delta\mu^s_{ik})\right|$$

[Equation 1]
Wherein i a Reference Solvent,
j are Solvent Candidates,
k is a Solute,
Sij Denotes A Similarity Between the Reference Solvent i and the Solvent Candidates j,
$\Delta\mu^s_{jk}$ Denotes a Standardized Value of $\Delta\mu_{jk}$,
$\Delta\mu_{jk}$ Denotes a Mixing Energy of the Solvent Candidates j for the Solute k,
$\Delta\mu^s_{ik}$ Denotes a Standardized Value of $\Delta\mu_{ik}$, and
$\Delta\mu_{ik}$ Denotes a Mixing Energy of the Reference Solvent i for the Solute k.

METHOD FOR SELECTING ALTERNATIVE SOLVENT

CROSS-REFERENCE TO RELATED APPLICATIONS

The present application is a national phase entry under 35 U.S.C. § 371 of International Application No. PCT/KR2018/008257 filed Jul. 23, 2018, which claims priority from Korean Patent Application No. 10-2017-0111893, filed on Sep. 1, 2017, the entire disclosures of which are incorporated herein by reference.

BACKGROUND OF THE INVENTION

1. Field of the Invention

The present invention relates to a method for selecting alternative solvents having properties similar to those of a reference solvent, and provides a method for selecting alternative solvents based on the similarity with the reference solvent and the compatibility with a solute as factors.

2. Description of the Related Art

Compared with other methods such as deposition, the method of manufacturing materials using a solution process is the most widely used method because the process is relatively simple, the physical properties are easy to control, and the manufacturing cost is very low. In this case, one of the important factors which influence performance of the solution process is the solvent used to prepare the solution used in the process. However, some of the conventionally used solvents may require replacement with other solvents because of environmental issues, process safety issues, and improvement of yield. The process of finding alternative solvents that are similar in properties to those conventionally used among many solvents requires complicated experiments that takes a lot of time, effort, and resources. Accordingly, among many solvents, there is a need for a method for easily and quickly finding alternative solvents having properties similar to those of conventional solvents.

The properties required for such alternative solvents are compatibility with each of a plurality of solutes and similarity with the conventionally used solvents. In order to facilitate the synthesis and purification of organic molecules, the compatibility of the solvents with each solute (reactant and product) plays an important role, and compatibility with such solute is a basis for estimating the dissolving ability of the solvents.

The dissolving ability of the solvents may be inferred by calculating the mixing energy of the solvents with respect to the solute and the similarity with the conventionally used solvents may be estimated by quantifying the similarity of the respective sigma potentials of the solvents. For example, the reference [A. Filly et al, LWT-Food Science and Technology, April 2015, Volume 61, Issue 1, pp. 33-40] discloses methods for selecting alternative solvents for n-hexane for food flavor extraction by COSMO-RS (Conductor-like Screening Model for Real Solvents) by using a statistical thermodynamic approach based on quantum chemical calculation results.

The inventors have been able to provide a method for selecting alternative solvents similar to the conventionally used solvents by using the physical quantity to be calculated and the specific model equation via the COSMO-RS theory.

SUMMARY OF THE INVENTION

The present invention provides a method for selecting solvents that may replace the conventionally used solvents.

In order to solve the above problems, the present invention provides a method for simply and rapidly selecting alternative solvents for the conventionally used solvents for synthesis and purification of organic molecules.

Specifically, the present invention provides a method for selecting alternative solvents, comprising calculating and standardizing the mixing energy of a reference solvent and solvent candidates for a solute, and calculating the di value of the solvent candidates by substituting the similarity of the solvent candidates to the reference solvent calculated by using the sigma potentials of the reference solvent and the solvent candidates into Equation 1:

$$d_{ij}=|(1-S_{ij},\Delta\mu^s_{j1}-\Delta\mu^s_{i1},\Delta\mu^s_{j2}-\Delta\mu^s_{i2},\ldots,\Delta\mu^s_{jk}-\Delta\mu^s_{ik})| \quad \text{[Equation 1]}$$

wherein i is the kind of the reference solvent, j is the kinds of the solvent candidates, k is the kind of the solute, $S_{ij}$ denotes the similarity between the reference solvent i and the solvent candidates j, $\Delta\mu^s_{jk}$ denotes a standardized value of $\Delta\mu_{jk}$, $\Delta\mu_{jk}$ denotes the mixing energy of the solvent candidates j for the solute k, $\Delta\mu^s_{ik}$ denotes the standardized value of $\Delta\mu_{ik}$, and $\Delta\mu_{ik}$ denotes the mixing energy of the reference solvent i for the solute k.

According to one embodiment, $S_{ij}$ in Equation 1 may be calculated according to Equation 2:

$$S_{ij} = \exp\left(-\sum_{m=-0.02}^{m=+0.02}|\mu_i(\sigma_m)-\mu_j(\sigma_m)|\right), \quad \text{[Equation 2]}$$

wherein $\mu_i(\sigma_m)$ denotes the sigma potential of the reference solvent i, and $\mu_j(\sigma_m)$ denotes the sigma potential of the solvent candidates j.

According to one embodiment, $\Delta\mu^s_{jk}$ in Equation 1 may be calculated according to Equation 3:

$$\Delta\mu^2_{jk}=(\Delta\mu_{jk}-M_k)/\sigma_k \quad \text{[Equation 3]}$$

wherein $\Delta\mu_{jk}$ denotes the mixing energy of the solvent candidates j for the solute k, $M_k$ denotes an average of $\{\Delta\mu_{jk}\}$, $\sigma_k$ denotes a standard deviation, and $\Delta\mu^s_{jk}$ denotes the standardized value of $\Delta\mu_{jk}$.

According to one embodiment, $S_{ij}$ may be a real number from 0.0 to 1.0 and $\Delta\mu_{jk}$ may be a real number from −20.0 to 20.0.

According to one embodiment, the $d_{ij}$ may be a real number between 0.0 and 11.0, and the smaller the value, the more similar to the reference solvent.

According to one embodiment, solvents in which the $d_{ij}$ is less than or equal to a certain value ($d_{cut}$), for example, solvents having a $d_{cut}$ of from 0.0 to 10.0 may be selected alternative solvents.

According to one embodiment, the reference solvent may be selected from the group consisting of xylene, acetone, chloroform, methyl ethyl ketone (MEK), methyl isobutyl ketone (MIBK), ethyl acetate (EA), butyl acetate, cyclohexanone, propylene glycol methyl ether acetate (PGMEA), dioxane, N-methylpyrrolidone (NMP), dimethylformamide (DMF), N,N-dimethylacetamide, dimethylsulfoxide, cyclopentanone, N,N-dimethylpropanamide, N,N-diethylformamide, 1-ethyl-2-pyrrolidinone, tetramethylurea, nitrobenzene, pyridine, γ-butyrolactone, 2-methylpyridine, 1,2-dimethoxyethane, 3-methyl-2-oxazolidone, 4-methylpyridine, cyclohexanone, 2-methylpyrazine, 1-vinyl-2-pyrrolidinone, 1,2-diaminoethane, 1-methylimidazole, thiazole, n-propyl acetate, 4,6-dimethylpyrimidine, isopropyl acetate, pyrimidine, aniline, 3-pyridinecarboxaldehyde, 2-(dimethylamino)-ethanol, isobutyl nitrate, 2,4-dimethylpyridine, acetic acid phenylmethyl ester, benzonitrile, 1,4-butanediamine, n-butyl acetate, benzyl alcohol, 1-methyl-1H-indole, N,N-diethyl-m-toluamide, 2-methylquinoline, 1H-indene, n-pentylacetate, 1-indanol, toluene, 1-methoxynaphthalene, propanol, ethoxybenzene, 1-methylnaphthalene, 2-butoxyethanol, 1,4-dimethylbenzene, 1,2-dimethylnaphthalene, 1-butanol, indane, 3-phenoxy toluene, 3-pentanol and the like.

According to one embodiment, the alternative solvents may be selected from the group consisting of oxetane, 1-methylimidazole, 1,3-dimethyl-2-imidazolidinone, 2-methylpyridine 1-oxide, tetramethylurea, xylene, acetone, chloroform, methyl ethyl ketone (MEK), methyl isobutyl ketone (MIBK), ethyl acetate (EA), butyl acetate, cyclohexanone, propylene glycol methyl ether acetate (PGMEA), dioxane, N-methylpyrrolidone (NMP), dimethylformamide (DMF), N,N-dimethylacetamide, dimethylsulfoxide, cyclopentanone, N,N-dimethylpropanamide, N,N-diethylformamide, 1-ethyl-2-pyrrolidinone, tetramethylurea, nitrobenzene, pyridine, γ-butyrolactone, 2-methylpyridine, 1,2-dimethoxyethane, 3-methyl-2-oxazolidone, 4-methylpyridine, cyclohexanone, 2-methylpyrazine, 1-vinyl-2-pyrrolidinone, 1,2-diaminoethane, 1-methylimidazole, thiazole, n-propyl acetate, 4,6-dimethylpyrimidine, isopropyl acetate, pyrimidine, aniline, 3-pyridinecarboxaldehyde, 2-(dimethylamino)-ethanol, isobutyl nitrate, 2,4-dimethylpyridine, acetic acid phenylmethyl ester, benzonitrile, 1,4-butanediamine, n-butyl acetate, benzyl alcohol, 1-methyl-1H-indole, N,N-diethyl-m-toluamide, 2-methylquinoline, 1H-indene, n-pentyl acetate, 1-indanol, toluene, 1-methoxynaphthalene, propanol, ethoxybenzene, 1-methylnaphthalene, 2-butoxyethanol, 1,4-dimethylbenzene, 1,2-dimethylnaphthalene, 1-butanol, indane, 3-phenoxy toluene, 3-pentanol, and the like.

The details of other embodiments of the present invention are included in the following detailed description.

According to the method of the present invention, it is possible to quickly select alternative solvents having properties similar to those of the conventionally used solvents among a number of candidate solvents through simple calculation methods, thereby saving time, effort, and resources consumed by complicated experiments.

BRIEF DESCRIPTION OF THE DRAWINGS

FIG. 1 is a graph showing the values obtained by standardizing the mixing energy of a reference solvent C (Solvent C) and solvent candidates (Candidates) for Solute A and Solute B according to an embodiment of the present invention.

FIG. 2 is a graph showing the similarity of the sigma potential between the reference solvent C (Solvent C) and the solvent candidates (Candidates) according to an embodiment of the present invention.

FIG. 3 is a flowchart schematically illustrating a method of selecting alternative solvents having properties similar to those of a reference solvent according to an embodiment of the present invention.

DETAILED DESCRIPTION OF THE INVENTION

The present invention will now be described in detail.

The present invention may be subject to various modifications and may have various embodiments, and specific embodiments are to be exemplified. It is to be understood, however, that the intention is not to limit the invention to the particular embodiments, but to cover all modifications, equivalents, and alternatives falling within the spirit and scope of the invention. In the following description of the present invention, detailed description of known functions will be omitted if it is determined that it may obscure the gist of the present invention.

When certain solvents used for synthesis or purification of organic molecules are to be replaced with another solvents due to environment, safety, etc., alternative solvents having properties similar to those of the conventionally used solvents may be selected.

According to the present invention, it is possible to save efforts, time, resources, etc. required for finding alternative solvents having similar properties to those of the conventionally used solvents among many solvents.

Specifically, the present invention provides a method for selecting alternative solvents, comprising calculating and standardizing the mixing energy of a reference solvent and solvent candidates for a solute, and calculating the di value of the solvent candidates by substituting the similarity of the solvent candidates to the reference solvent calculated by using the sigma potentials of the reference solvent and the solvent candidates into Equation 1:

$$d_{ij} = |(1-S_{ij}, \Delta\mu^s_{j1} - \Delta\mu^s_{i1}, \Delta\mu^s_{j2} - \Delta\mu^s_{i2}, \ldots, \Delta\mu^s_{jk} - \Delta\mu^s_{ik})|$$
[Equation 1]

wherein i is the kind of the reference solvent, j is the kinds of the solvent candidates, k is the kind of the solute, $S_{ij}$ denotes the similarity between the reference solvent i and the solvent candidates j, $\Delta\mu^s_{jk}$ denotes a standardized value of $\Delta\mu_{jk}$, $\Delta\mu_{jk}$ denotes the mixing energy of the solvent candidates j for the solute k, $\Delta\mu^s_{ik}$ denotes the standardized value of $\Delta\mu_{ik}$, and $\Delta\mu_{ik}$ denotes the mixing energy of the reference solvent i for the solute k.

According to one embodiment, $S_{ij}$ in Equation 1 may be calculated according to Equation 2:

$$S_{ij} = \exp\left(-\sum_{m=-0.02}^{m=+0.02} |\mu_i(\sigma_m) - \mu_j(\sigma_m)|\right),$$
[Equation 2]

wherein $\mu_i(\sigma_m)$ denotes the sigma potential of the reference solvent i, and $\mu_j(\sigma_m)$ denotes the sigma potential of the solvent candidates j.

According to one embodiment, $\Delta\mu^s_{jk}$ in Equation 1 may be calculated according to Equation 3:

$$\Delta\mu^s_{jk} = (\Delta\mu_{jk} - M_k)/\sigma_k$$
[Equation 3]

wherein $\Delta\mu_{jk}$ denotes the mixing energy of the solvent candidates j for the solute k, $M_k$ denotes an average of $\{\Delta\mu_{jk}\}$, $\sigma_k$ denotes a standard deviation, and $\Delta\mu^s_{jk}$ denotes the standardized value of $\Delta\mu_{jk}$.

According to one embodiment, $S_{ij}$ may be a real number from 0.0 to 1.0 and $\Delta\mu_{jk}$ may be a real number from −20.0 to 20.0.

According to one embodiment, the $d_{ij}$ may be a real number between 0.0 and 11.0, for example a real number between 0.0001 and 0.9, and the smaller the value, the more similar to the reference solvent.

According to one embodiment, solvents in which the $d_{ij}$ is less than or equal to a certain value ($d_{cut}$), for example, solvents having a $d_{cut}$ of from 0.0 to 10.0 may be selected as alternative solvents.

Hereinafter, embodiments of the present invention will be described in detail in order to facilitate those skilled in the art to which the present invention pertains. However, the present invention may be embodied with various modifications and variations and is not limited to the embodiments described herein.

Example

In the example, solvent candidates similar to the reference solvent C in terms of the properties for Solute A and Solute B, respectively, were selected. Solute A, Solute B, and Reference Solvent C used are shown in Table 1 below.

TABLE 1

| Solute A | 4,4'-methylenediphenol |
|---|---|
| Solute B | 4,4'-((methylenebis(4,1-phenylene))bis(oxy))diphthalonitrile |
| Reference Solvent C | dimethylformamide |

Solvent candidates were selected from a solvent library consisting of about 1800 kinds of solvents, including the solvents commonly used in the synthesis process, which exist in a liquid state at a room temperature, as follows.

1. The similarity values ($S_{ij}$) of the solvents in the solvent library to Reference Solvent C were calculated according to Equation 2 above by using the sigma potentials of the reference solvent and the solvents of the solvent library.

2. The mixing energy values of the solvents in the solvent library for Solute A and Solute B were calculated according to Equation 3 above by applying the COSMO-RS theory.

3. The mixing energy values of the solvents calculated in item 2 above were standardized, respectively.

4. The distance values ($d_{ij}$) between Reference Solvent C and the respective solvents of the solvent library on the hyperspace consisting of the sigma potential similarity values ($S_{ij}$) of the solvents and the standardized mixing energy values were calculated according to Equation 1 above. The solvents having the $d_{ij}$ values of 0.0 to 10.0 were selected as solvent candidates. The $d_{ij}$ values of the solvent candidates are shown in Table 2 below.

TABLE 2

| | Solvents | $d_{ij}$ value |
|---|---|---|
| Reference Solvent | dimethylformamide | 0.0 |
| Solvent Candidates | N,N-dimethylacetamide | 0.452 |
| | N-methyl-2-pyrrolidinone | 0.604 |
| | oxetane | 0.743 |
| | 4,6-dimethylpyrimidine | 0.758 |
| | N,N-dimethylpropaneamide | 0.791 |
| | pyridine | 0.810 |
| | 1-methylimidazole | 0.819 |
| | 1,3-dimethyl-2-imidazolidinone | 0.820 |
| | N,N-diethylformamide | 0.824 |
| | 2-methylpyrazine | 0.841 |
| | 2-methylpyridine 1-oxide | 0.845 |
| | tetramethylurea | 0.887 |

As shown in Table 2 above, it is confirmed that N,N-dimethylacetamide, N-methyl-2-pyrrolidinone, oxetane, 4,6-dimethylpyrimidine, N,N-dimethylpropanamide, pyridine, 1-methylimidazole, 1,3-dimethyl-2-imidazolidinone, N,N-diethylformamide, 2-methylpyrazine, 2-methylpyridine 1-oxide and tetramethylurea in the solvent library are the solvents having distance values ($d_{cut}$) of 0.9 or less, which are alternative solvents to Reference Solvent C.

The standardized values of the mixing energy of Reference Solvent C and the solvent candidates for the solutes A and B are shown in FIG. 1. In FIG. 1, "Solvent C" refers to Reference Solvent C and "Candidates" refers to the solvent candidates.

Also, a graph showing the sigma potential similarity between Reference Solvent C and the solvent candidates is shown in FIG. 2. In FIG. 2, "Solvent C" refers to Reference Solvent C and "Candidates" refers to the solvent candidates.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A method for selecting alternative solvents having properties similar to those of a conventionally used solvent without complicated experiments, comprising:
calculating and standardizing a mixing energy of a reference solvent and solvent candidates for a solute, and
calculating a $d_{ij}$ value of the solvent candidates by substituting a similarity of the solvent candidates to the reference solvent calculated by using the sigma potentials of the reference solvent and the solvent candidates into Equation 1:

$$d_{ij}=|(1-S_{ij},\Delta\mu^s_{j1}-\Delta\mu^s_{i1},\Delta\mu^s_{j2}-\Delta\mu^s_{i2},\ldots,\Delta\mu_{jk}{}^2-\Delta\mu^s_{ik})| \quad [\text{Equation 1}],$$

wherein i a reference solvent,
j are solvent candidates,
k is a solute,
$S_{ij}$ denotes a similarity between the reference solvent i and the solvent candidates j,
$\Delta\mu^s_{jk}$ denotes a standardized value of $\Delta\mu_{jk}$,
$\Delta\mu_{jk}$ denotes a mixing energy of the solvent candidates j for the solute k,
$\Delta\mu^s_{ik}$ denotes a standardized value of $\Delta\mu_{ik}$, and
$\Delta\mu_{ik}$ denotes a mixing energy of the reference solvent i for the solute k.

2. The method for selecting alternative solvents according to claim 1, wherein $S_{ij}$ in Equation 1 is calculated according to Equation 2:

$$S_{ij} = \exp\left(-\sum_{m=-0.02}^{m=+0.02}|\mu_i(\sigma_m)-\mu_j(\sigma_m)|\right), \quad [\text{Equation 2}]$$

wherein $\mu_i(\sigma_m)$ denotes a sigma potential of the reference solvent i, and
$\mu_j(\sigma_m)$ denotes a sigma potential of the solvent candidates j.

3. The method for selecting alternative solvents according to claim 1, wherein $\Delta\mu^s_{jk}$ in Equation 1 is calculated according to Equation 3:

$$\Delta\mu^2_{jk}=(\Delta\mu_{jk}-M_k)/\sigma_k \quad [\text{Equation 3}]$$

wherein $\Delta\mu_{jk}$ denotes a mixing energy of the solvent candidates j for the solute k,
$M_k$ denotes an average of $\{\Delta\mu_{jk}\}$,
$\sigma_k$ denotes a standard deviation, and
$\Delta\mu^s_{jk}$ denotes the standardized value of $\Delta\mu_{jk}$.

4. The method for selecting alternative solvents according to claim 1, wherein $S_{ij}$ in Equation 1 is a real number from 0.0 to 1.0.

5. The method for selecting alternative solvents according to claim 1, wherein $\Delta\mu_{jk}$ in Equation 1 is a real number from −20.0 to 20.0.

6. The method for selecting alternative solvents according to claim 1, wherein $d_{ij}$ in Equation 1 is between 0.0 and 11.0.

7. The method for selecting alternative solvents according to claim 1, wherein the solvents having a $d_{ij}$ of from 0.0 to 10.0 ($d_{cut}$) are selected as the alternative solvents.

8. The method for selecting alternative solvents according to claim 1, wherein the reference solvent is selected from the group consisting of xylene, acetone, chloroform, methyl ethyl ketone (MEK), methyl isobutyl ketone (MIBK), ethyl acetate (EA), butyl acetate, cyclohexanone, propylene glycol methyl ether acetate (PGMEA), dioxane, N-methylpyrrolidone (NMP), dimethylformamide (DMF), N,N-dimethylacetamide, dimethylsulfoxide, cyclopentanone, N,N-dimethylpropanamide, N,N-diethylformamide, 1-ethyl-2-pyrrolidinone, tetramethylurea, nitrobenzene, pyridine, γ-butyrolactone, 2-methylpyridine, 1,2-dimethoxyethane, 3-methyl-2-oxazolidone, 4-methylpyridine, cyclohexanone, 2-methylpyrazine, 1-vinyl-2-pyrrolidinone, 1,2-diaminoethane, 1-methylimidazole, thiazole, n-propyl acetate, 4,6-dimethylpyrimidine, isopropyl acetate, pyrimidine, aniline, 3-pyridinecarboxaldehyde, 2-(dimethylamino)-ethanol, isobutyl nitrate, 2,4-dimethylpyridine, acetic acid phenylmethyl ester, benzonitrile, 1,4-butanediamine, n-butyl acetate, benzyl alcohol, 1-methyl-1H-indole, N,N-diethyl-m-toluamide, 2-methyl-quinoline, 1H-indene, n-pentylacetate, 1-indanol, toluene, 1-methoxynaphthalene, propanol, ethoxybenzene, 1-methylnaphthalene, 2-butoxyethanol, 1,4-dimethylbenzene, 1,2-dimethylnaphthalene, 1-butanol, indane, 3-phenoxy toluene and 3-pentanol.

9. The method for selecting alternative solvents according to claim 1, wherein the alternative solvents are selected from the group consisting of oxetane, 1-methylimidazole, 1,3-dimethyl-2-imidazolidinone, 2-methylpyridine 1-oxide, tetramethylurea, xylene, acetone, chloroform, methyl ethyl ketone (MEK), methyl isobutyl ketone (MIBK), ethyl acetate (EA), butyl acetate, cyclohexanone, propylene glycol methyl ether acetate (PGMEA), dioxane, N-methylpyrrolidone (NMP), dimethylformamide (DMF), N,N-dimethylacetamide, dimethylsulfoxide, cyclopentanone, N,N-dimethylpropanamide, N,N-diethylformamide, 1-ethyl-2-pyrrolidinone, tetramethylurea, nitrobenzene, pyridine, γ-butyrolactone, 2-methylpyridine, 1,2-dimethoxyethane, 3-methyl-2-oxazolidone, 4-methylpyridine, cyclohexanone, 2-methylpyrazine, 1-vinyl-2-pyrrolidinone, 1,2-diaminoethane, 1-methylimidazole, thiazole, n-propyl acetate, 4,6-dimethylpyrimidine, isopropyl acetate, pyrimidine, aniline, 3-pyridinecarboxaldehyde, 2-(dimethylamino)-ethanol, isobutyl nitrate, 2,4-dimethylpyridine, acetic acid phenylmethyl ester, benzonitrile, 1,4-butanediamine, n-butyl acetate, benzyl alcohol, 1-methyl-1H-indole, N,N-diethyl-m-toluamide, 2-methyl-quinoline, 1H-indene, n-pentyl acetate, 1-indanol, toluene, 1-methoxynaphthalene, propanol, ethoxybenzene, 1-methylnaphthalene, 2-butoxyethanol, 1,4-dimethylbenzene, 1,2-dimethylnaphthalene, 1-butanol, indane, 3-phenoxy toluene and 3-pentanol.

\* \* \* \* \*